United States Patent [19]
Hemmati

[11] Patent Number: 5,747,351
[45] Date of Patent: May 5, 1998

[54] IMMUNOCHEMICAL-BASED TEST DEVICE WITH LIFT AND TWIST SPECIMEN FULL TAB

[75] Inventor: Goodarz Sahneh Hemmati, Santa Clara, Calif.

[73] Assignee: SmithKline Diagnostics, Inc., Palo Alto, Calif.

[21] Appl. No.: 480,572

[22] Filed: Jun. 7, 1995

[51] Int. Cl.⁶ .................................................. G01N 33/543
[52] U.S. Cl. ................... 436/514; 422/56; 422/57; 422/58; 422/274; 422/275; 422/276; 422/61; 435/294.1; 435/7.1; 435/970; 435/975; 436/518; 436/809; 436/810
[58] Field of Search ........................ 422/56, 57, 58, 422/274, 275, 276, 61; 435/294.1, 970, 975, 7.1; 436/518, 809, 514, 810

[56] References Cited

U.S. PATENT DOCUMENTS

| | | |
|---|---|---|
| 1,926,299 | 9/1933 | Monk. |
| 3,078,031 | 2/1963 | Kauffeld. |
| 3,122,301 | 2/1964 | Barr. |
| 3,186,623 | 6/1965 | Guyer. |
| 3,307,770 | 3/1967 | Wysocki. |
| 3,951,332 | 4/1976 | Torbeck. |
| 4,225,557 | 9/1980 | Hartl et al.. |
| 4,285,461 | 8/1981 | Meyers. |
| 4,464,552 | 8/1984 | Pawlowski. |
| 4,717,656 | 1/1988 | Swanisung .................. 435/7 |
| 4,789,629 | 12/1988 | Baker et al. ................. 435/7 |
| 4,803,048 | 2/1989 | Nason. |
| 4,976,354 | 12/1990 | Levy. |
| 5,143,210 | 9/1992 | Warwick et al.. |
| 5,182,191 | 1/1993 | Fan et al. ................... 435/7.9 |
| 5,441,698 | 8/1995 | Norell ....................... 422/58 |

FOREIGN PATENT DOCUMENTS

| | | |
|---|---|---|
| 0 653 639 A1 | 5/1995 | European Pat. Off.. |
| 677473 A5 | 5/1991 | Germany. |
| 4341862 A1 | 6/1994 | Germany. |
| WO 94/24563 | 10/1994 | WIPO. |

*Primary Examiner*—Christopher L. Chin
*Assistant Examiner*—Bao-Thuy L. Nguyen
*Attorney, Agent, or Firm*—William H. May; Arnold Grant; Merchant & Gould

[57] ABSTRACT

A chromatographic assay test device for use with immunoassays. The test device has a sample collection member pivotally coupled to a test strip receiving member. The sample collection member has a window for applying a test sample to a pad accessible through the window and the pad is repositionable to an inverted position to contact a chromatographic member inserted into the test device. The chromatographic member is then brought into opposition to the sample collection member thus improving test performance by reducing the manipulation of samples. The test device is constructed from five interconnected panels which are die cut from SBS cardboard. The first panel has a window for inserting a test strip and the second panel has a window for viewing the test strip during the test procedure. The third panel has the repositionable pad section. The fourth panel has a window for applying the test sample and the fifth panel covers the test sample window. The first and second panels are coupled to form a first planar member and the third and fourth panels are coupled to form the sample collection member. The fifth panel includes a reusable adhesive for securing the fifth panel over the sample window in the fourth panel.

22 Claims, 4 Drawing Sheets

5,747,351

IMMUNOCHEMICAL-BASED TEST DEVICE WITH LIFT AND TWIST SPECIMEN PULL TAB

CROSS-REFERENCE TO RELATED APPLICATIONS

This application is related to application Ser. No. 08/119,466, entitled "Bevel Closure and Device", filed on Sep. 10, 1993 by Joyce Norell now U.S. Pat. No. 5,441,698, and to application Ser. No. 08/194,793, entitled "Assay Device", filed on Feb. 10, 1994 by H. M. Chandler, now pending, which is a continuation of application Ser. No. 07/888,831, entitled "Assay Device", filed on May 27, 1992 by H. M. Chandler, now abandoned, all of which are assigned to the assignee of this application, and are hereby incorporated by reference.

BACKGROUND OF THE INVENTION

This invention relates in general to an immunochemical-based test method and apparatus, and more specifically, to an integrated housing and sample collection method and apparatus having a lift and twist specimen pull tab.

Among the many analytical systems used for detection and/or determination of analytes, particularly analytes of biological interest, are chromatographic assay systems. Such chromatographic systems are frequently used by physicians and medical technicians for rapid in-office diagnosis and therapeutic monitoring of a variety of conditions and disorders. They are also increasingly used by patients themselves for at-home monitoring of such conditions and disorders. Among the most important of such systems are the "thin layer" systems in which a solvent moves across a thin, flat absorbent medium.

Although useful, currently available chromatographic techniques using test strips have a number of drawbacks. Many samples, such as fecal samples, contain particulate matter that can clog the pores of the chromatographic medium, greatly hindering the immunochromatographic process. Other samples, such as blood, contain cells and colored components that make it difficult to read the test. Even if the sample does not create interference, it is frequently difficult with existing chromatographic test devices to apply the sample to the chromatographic medium so that the sample front moves uniformly through the chromatographic medium to insure that the sample reaches the area where binding is to occur in a uniform, straight-line manner.

Sample preparation and waste generation are responsible for other problems with currently available devices and techniques for immunochromatography. The increased prevalence of diseases spread by infected blood and blood fractions, such as AIDS and hepatitis, has exacerbated these problems. It is rarely possible to apply a sample (such as feces) or a sampling device (such as a throat swab) directly to the chromatographic medium. Several extraction and pretreatment reactions are usually required before the sample can be applied to the chromatographic medium. These reactions have typically been carried out by the physician or technician performing the test in several small vessels, such as test tubes or microfuge tubes, requiring the use of transfer devices such as pipettes. Each of these devices is then contaminated and must be disposed of using special precautions so that workers or people who may inadvertently come into contact with the waste do not become contaminated.

Improved chromatographic devices for the performance of immunochromatographic assays or other analogous assays have been developed. Such devices are capable of receiving a possibly contaminated sample or a sample preparation device directly so as to eliminate the need for extraction vessels and transfer devices. Such devices include a test strip and are able to deliver the sample to the chromatographic medium uniformly and evenly to improve accuracy and precision of the tests. This aspect of assay devices is particularly important in avoiding false negatives and false positives.

However, several steps are required in performing the test. Samples must first be collected and applied to a collection device. After the required number of samples are collected, the collection container is closed and forwarded to a doctor or a laboratory for testing. Before the lab can test the samples, a specimen has to be taken from the collection container and placed in an assay device.

These assay devices include a conductive barrier attached to an opposable component of a device containing at least two opposable components. The assay devices make use of pressure to transfer fluid from one opposable component to another opposable component, and also to drive fluid through the chromatographic medium. The pressure not only speeds up the operation of the device, but allows the performance of additional steps such as extraction steps to remove interfering particulate components within a single device. The pressure is generated by holding the opposable components together with engagers such as interlocking elements on each of the opposable components. Preferably, a predetermined pressure is applied to ensure the optimum performance of each step of the assay procedure.

It can be seen then that there is a need for a test method and device which improves test performance by reducing manipulation of samples.

It can also be seen that there is a need for a simplified method and apparatus for carrying out the test procedure.

It can also be seen that there is a need to reduce cost by minimizing the number of parts required and by reducing the operational steps.

It can also be seen that there is a need to improve manufacturability and quality of test devices by reducing the number of components and the number of manufacturing steps.

It can also be seen that there is a need to encourage testing by reducing the complexity of the test.

SUMMARY OF THE INVENTION

To overcome the limitations in the prior art described above, and to overcome other limitations that will become apparent upon reading and understanding the present specification, the present invention discloses a immunochemical-based test device having a sample collection member pivotally coupled to a test strip member. The sample collection member has a window for applying a test sample to a pad accessible through the window and the pad is rotatable to an inverted position to contact a chromatographic member as it is brought into opposition to the sample collection member.

The present invention solves the above-described problems by providing a test method and device which improves test performance by reducing manipulation of samples.

A system in accordance with the principles of the present invention comprises a test strip receiving member for receiving a chromatographic test strip and having an external viewing window, a sample collection member coupled to the test strip member, the sample collection member having a port for applying a test sample to an accessible pad. The pad is repositionable to an inverted position for contacting the chromatographic test strip as the test strip receiving member is brought into opposition to the sample collection member.

The test strip receiving member and the sample collection member are constructed from five interconnected panels. The first panel has a window for insertion of a test strip. The second panel has a window for viewing the test strip during the test procedure. The third panel has a perforated section having a specimen pad coupled to one side, the perforated section being repositionable to expose a collected sample deposited onto the specimen pad to the test strip. The fourth panel has a window for applying the test sample and the fifth panel forms a covering for the test sample window.

The fourth panel also includes a notch for facilitating the repositioning of the repositionable section of the third panel. The first and second panels are coupled to form a first planar member and the third and fourth panels are coupled to form a second planar member. The fifth panel includes a repositionable adhesive for securing the fifth panel over the sample window in the fourth panel.

The bodies of the panels or opposable components are preferably made of laminated cardboard that is sufficiently impervious to moisture to contain the liquids involved in the performance of the assay carried out by the device. Other cellulose-based materials, such as paperboard or solid bleached sulfite (SBS) can also be used. Alternatively, the bodies of the opposable components can be made of plastic that is impervious to moisture. A suitable plastic is a polycarbonate plastic such as Lexan™. In the preferred embodiment, the panels are die cut from SBS cardboard having a thickness of about 0.024 inches.

One aspect of the present invention is that the test device simplifies the method for carrying out the test procedure.

Another aspect of the present invention is that cost is reduced by minimizing the number of parts required and by reducing the operational steps.

Another aspect of the present invention is that manufacturability and quality of test devices are improved by reducing the number of components and the number of manufacturing steps.

Yet another aspect of the present invention is that testing is encouraged by reducing the complexity of the test.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there is illustrated and described specific examples of an apparatus in accordance with the invention.

BRIEF DESCRIPTION OF THE DRAWINGS

Referring now to the drawings in which like reference numbers represent corresponding parts throughout.

DETAILED DESCRIPTION OF THE INVENTION

In the following description, reference is made to the accompanying drawings which form a part hereof, and in which is shown by way of illustration the specific embodiment in which the invention may be practiced. It is to be understood that other embodiments may be utilized as structural changes may be made without departing from the scope of the present invention.

One aspect of the present invention comprises chromatographic assay devices particularly useful for the assay of analytes in biological samples. These devices are suitable for the direct application of biological samples, without preliminary extraction steps, and are constructed so as to reduce manipulation of test samples and simplify the test procedure.

Figure 1:
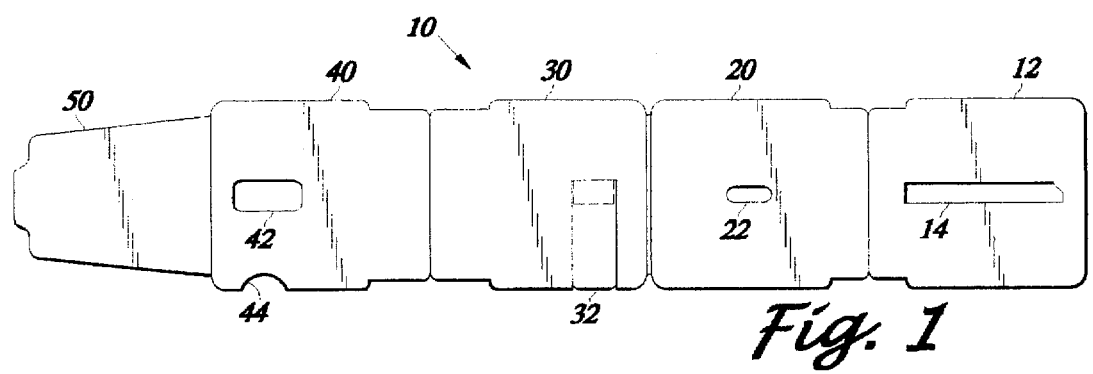
FIG. 1 illustrates an integrated housing of the invention as it is die cut.

FIG. 1 illustrates an integrated housing 10 of the invention as it is die cut. The integrated housing is preferably die cut from 0.024" thick SBS cardboard. However, it is to be understood that other materials could be used in manufacturing the invention. For example, the integrated housing could be formed from vinyl or may be produced using injection molding.

Initially, the integrated housing comprises five panels. The first panel 12 includes a window 14 for insertion of a test strip (not shown in FIG. 1, see FIG. 6). The second panel 20 includes a viewing window 22 for reading the test strip during the test procedure. The third panel 30 preferably comprises a perforated section 32 which may be lifted and twisted as explained more fully with reference to FIG. 7. The fourth panel 40 has a window or port 42 exposed centrally therein for applying the test sample. It is to be understood that the port 42 is not meant to be limited to any particular shape. The fourth panel also has a notch 44 cut along one of its sides which allows the lift and twist tab 32 of the third panel 30 to be more easily accessed. Finally, the fifth panel 50 functions as a cover for the test sample window 42.

Figure 2A:
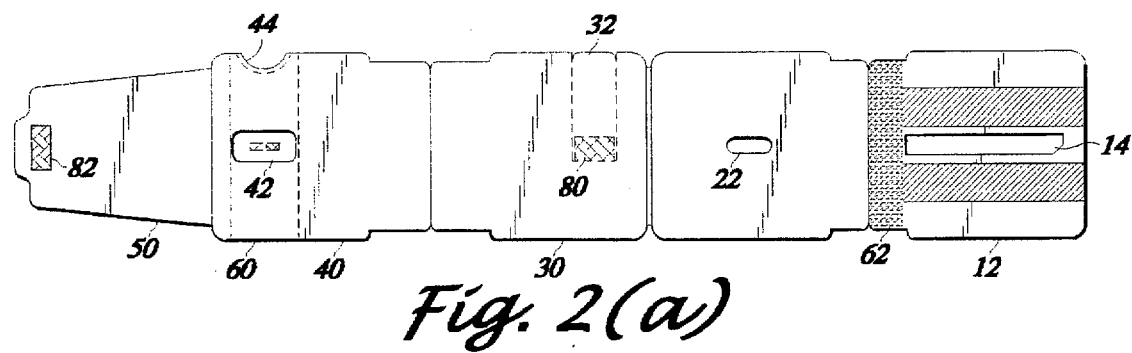
FIGS. 2(a)–2(b) illustrate the application of a sample metering panel to the fourth panel, a specimen pad to the third panel and the integration of the first and second panels.
Figure 2B:
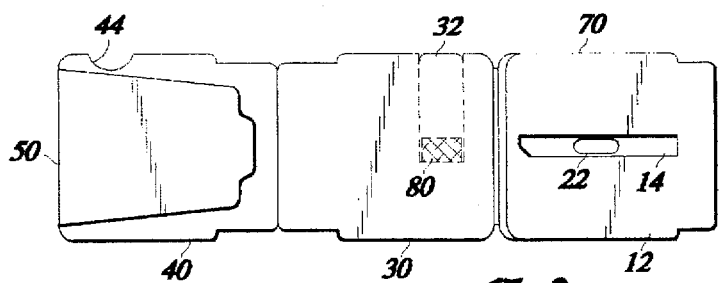

FIG. 2(a) illustrates a sample panel 60 applied to the fourth panel 40 in alignment with the sample window 42. Glue is applied to an area 62 of the first panel 12 as illustrated so that when the first panel 12 is folded over, the first panel 12 and second panel 20 form a first single planar member or planar test strip receiving member 70 as illustrated in FIG. 2(b). In addition, a specimen pad 80 is attached to the perforated repositionable tab 32 in the third panel 30. A reusable adhesive is applied to a section 82 at the end of the fifth panel 50 such that the fifth panel 50 may be temporarily affixed to the fourth panel 40 thereby covering the sample window 42. However, the nature of the reusable adhesive allows a patient/user to easily peel back the fifth panel 50 exposing the sample window 42. FIG. 2(b) illustrates the first 12 and fifth 50 panels in their folded positions over the second 20 and fourth 40 panels, respectively.

Figure 3A:
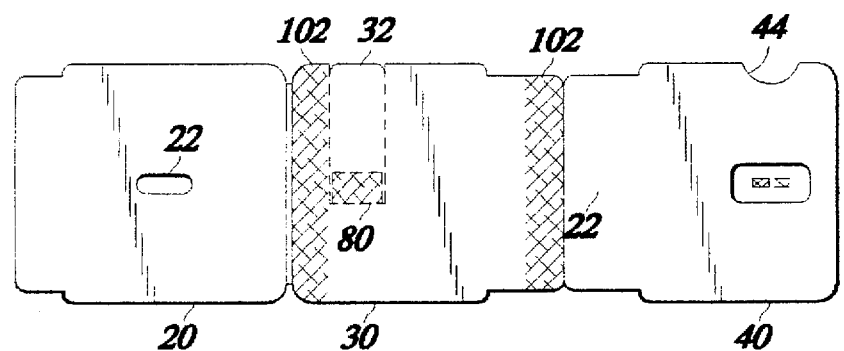
FIGS. 3(a)–3(b) illustrate the integration of the third and fourth panels.
Figure 3B:
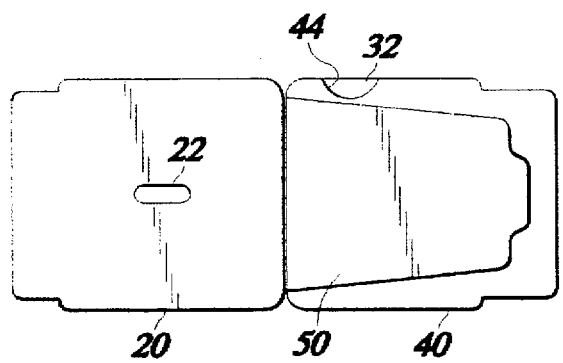

FIG. 3(a) illustrates the application of glue across the width 102 of the third panel 30 at each end. Thereafter, the fourth panel 40 and fifth 50 panel are folded over the third panel 30 as illustrated in FIG. 3(b). The third 30 and fourth 40 panels are thus combined to form a second planar member or sample collection member. Note that FIG. 3(b) illustrates the opposite side on the test device 10 as compared to FIG. 3(a). Also, FIG. 3(b) illustrates the lift and twist tab 32 protruding beyond the notch 44 cut in the fourth panel 40.

Figure 4:
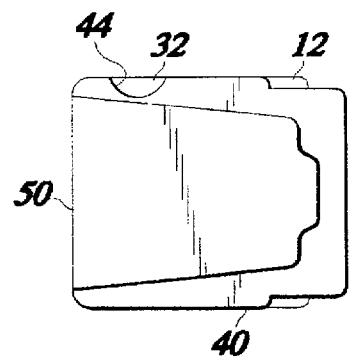
FIG. 4 illustrates the integrated immunochemical-based test device with lift and twist specimen pull tab.

Finally, FIG. 4 illustrates the compact test device wherein the first planar member formed by the first 12 and second 20 panels has been brought toward the second planar member formed by the third 30 and fourth 40 panels.

Figure 5:
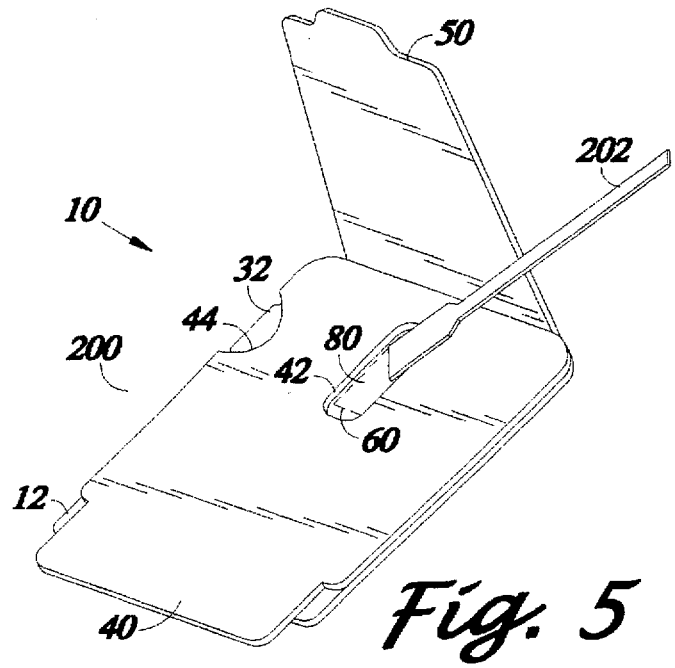
FIG. 5 illustrates the first step in the test procedure using the test device of the present invention.

FIG. 5 illustrates the first step 200 in the sample collection procedure. The fifth panel 50 is pulled away from the integrated housing 10 thereby exposing the sample well 42 and the sample metering panel 60 superimposed over the sample pad 80. After the patient/user opens the fifth panel 50, a sample is deposited to the sample well 42 using an applicator 202. The patient/user then closes the fifth panel 50 thereby allowing the integrated housing 10 to be forwarded to a physician or to a laboratory for carrying out the test procedure.

Figure 6:
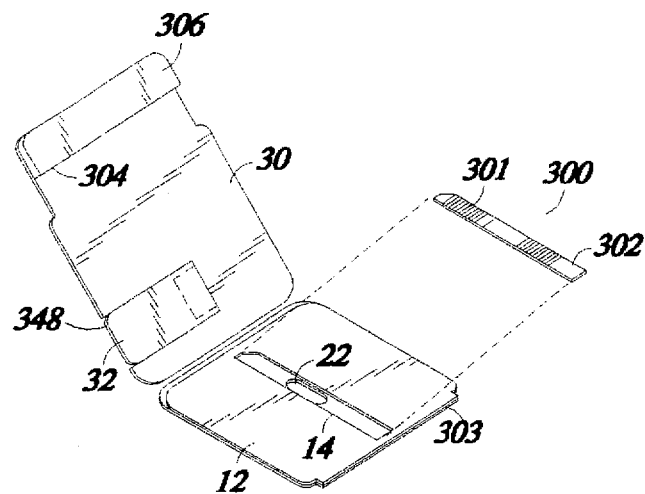
FIG. 6 illustrates the planar combination of the first and second panels being pulled away from the integrated housing structure so that a test strip may be inserted into the cut out in the first panel.

FIG. 6 illustrates the planar test strip receiving member, formed by the first 12 and second panels 20, being pulled away from the integrated housing structure 10 thereby exposing the test strip cut out 14 in the first panel 12. The physician or laboratory technician may install a test strip 300 into the invention at the cut out 14 of the first panel 12. The test strip 300 may be elongated having a first end 301 for engaging the specimen pad and a second end 302 distal from the first end 301.

The first and second planar member combinations may be held together by a tab-insert combination which is well known in the art, or preferably, by a latching mechanism formed by a beveled edge 303, formed at an edge of the planar combination of the first 12 and second panels 20, and an undercut edge 304 formed on a closure portion or planar fixed member 306 that is fixed to the third panel 30, as is disclosed in U.S. patent application Ser. No. 08/119,466, now U.S. Pat. No. 5,441,698 entitled "Bevel Closure and Device," referenced above.

Figure 7:
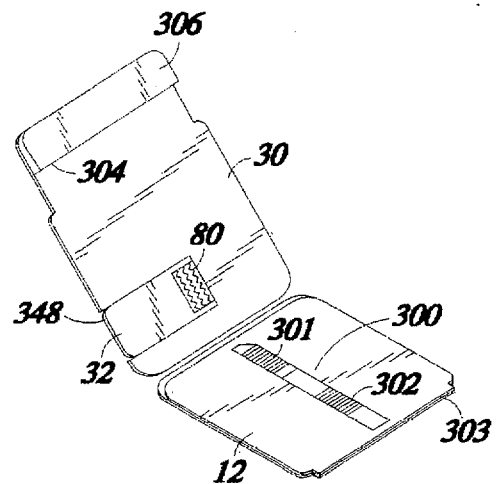
FIG. 7 illustrates the use of the lift and twist tab of the present invention.

FIG. 7 illustrates the use of the preferred embodiment of the repositionable tab 32. Alternatively, as discussed with reference to FIGS. 10 and 11, the specimen pad 80 may be fixedly secured to the planar combination formed by the third 30 and fourth 40 panels in the window (not shown in FIG. 7), and in alignment with test strip 300. However, certain disadvantages are inherent to a stationary pad. These disadvantages are discussed with reference to FIG. 8 below.

Referring to the preferred embodiment illustrated in FIG. 7, the physician or laboratory technician lifts the perforated specimen pull tab 32 away from the third panel 30 and twists the specimen pull tab 32 180° to an inverted position so that the specimen pad pull tab 32 may be refitted into a recessed area originally vacated by the specimen pad pull tab 32. The specimen pad pull tab 32 may or may not remain coupled to the third panel 30. Accordingly, the specimen pad 80 in the inverted position faces the test strip 300 and engages with the test strip 300 upon closure of the housing 10. However, it is to be understood that this embodiment is presented for illustration only and is not meant to limit the invention. Those skilled in the art will recognize that other embodiments incorporating the teaching of the present invention are possible without departing from the invention. For example, the outside edge 308 of the specimen pad pull tab 32 may be flipped over to the opposite side of the third panel 30 to an inverted position thereby exposing the specimen pad 80. In this embodiment, the position of the test strip window 14 may have to be offset so that the specimen pad 80 aligns with the test strip 300 in the flipped position.

Figure 8:
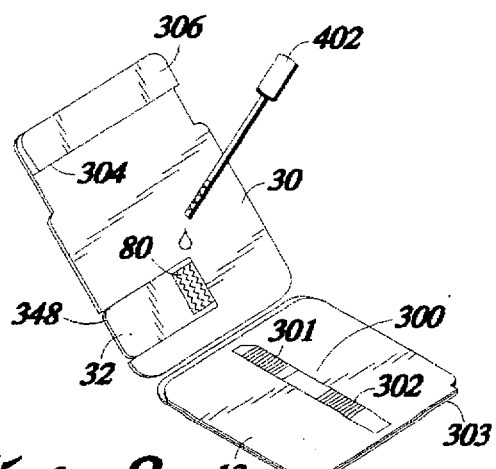
FIG. 8 illustrates a buffer being added to the specimen pad.

Referring now to FIG. 8, a buffer 402 is added to the specimen pad 80 to facilitate the interaction between the specimen pad 80 and the test strip 300 before the housing 10 is closed. The buffer when applied to the pad 80 permeates down into the pad 80 itself and thus does not negatively affect the test strip as the test strip is brought into opposition with the specimen pad 80. As is now readily apparent, the invention embodying a stationary specimen pad 80 will lead to the buffer, as it is applied to the sample side of the pad 80, permeating through the pad 80 and into the test strip 300 thereby negatively affecting the test by causing the sample front to move non-uniformly through the chromatographic test strip 300. Thus, the lift embodiment for positioning the pad 80 for engagement with the test strip 300 is preferred.

Figure 9:
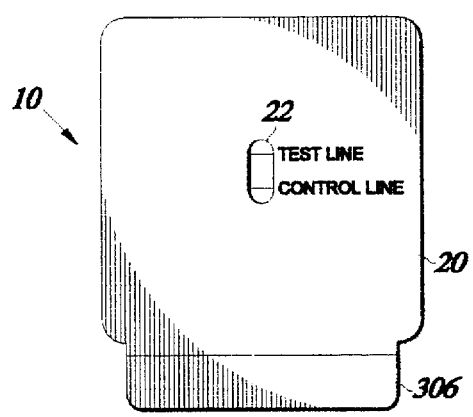
FIG. 9 illustrates the integrated test device after the unit is closed thereby allowing the specimen pad to engage the test strip.

FIG. 9 illustrates the integrated test device after the unit 10 is closed thereby allowing the specimen pad 80 to engage the test strip 300. The physician or lab technician may read the results of the test through the observation window 22 in the second panel 20.

Figure 10:
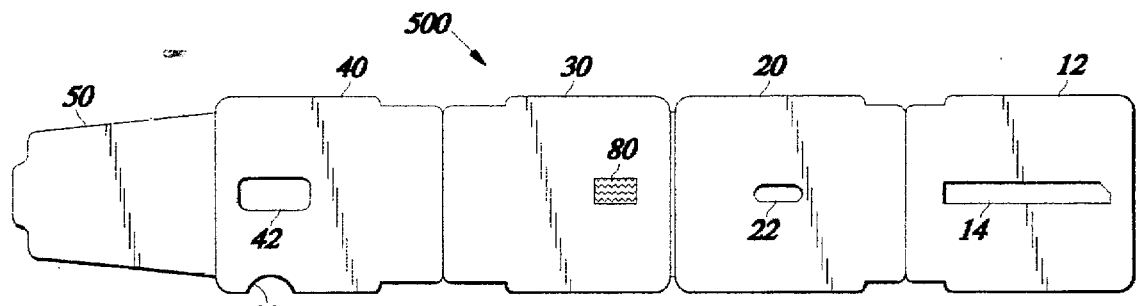
FIG. 10 illustrates an alternative embodiment of the housing die cut in accordance with the invention wherein the third panel has a specimen pad permanently disposed therein in alignment with the test strip.

FIG. 10 illustrates the alternative embodiment of the integrated housing 500 of the invention. The integrated housing 500 is die cut from 0.024" thick SBS cardboard to form five panels. However, in this embodiment, the third panel 30 has the stationary specimen pad 80 fixedly disposed therein in alignment with test strip 300.

Figure 11:
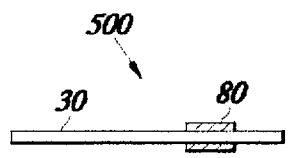
FIG. 11 illustrates the stationary specimen pad extending beyond the surface on each side of the third panel.

FIG. 11 illustrates a side view of the alternative embodiment 500 wherein the stationary specimen pad 80 extends beyond the surface of the third panel 30. Thus, the stationary specimen pad 80 is accessible through the window 42 in the fourth panel 40. However, since the pad 80 is stationary, the test sample applied to the specimen pad 80 must permeate to the side of the third panel 30 which engages the test strip member 300.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not with this detailed description, but rather by the claims appended hereto.

What is claimed is:

1. An immunochemical-based test device for insertion of a chromatographic member, comprising:

a test strip receiving member for inserting a chromatographic test strip therein, the test strip receiving member having an external viewing window to view the inserted chromatographic test strip; and a sample collection member coupled to the test strip receiving member, the sample collection member having a port for applying a test sample to an accessible pad located in a first position, the pad being repositionable to an inverted position, the pad forming a face section of the sample collection member for contacting the chromatographic test strip as the test strip receiving member is brought into opposition to the sample collection member.

2. The test device of claim 1 further comprising a window cover member for shielding the window of the sample collection member.

3. The test device of claim 1 wherein the pad is coupled to a perforated pull tab, the pull tab being pivoted from the sample collection member to form a pull tab recess area, twisted 180° and reushered into the recessed area to position the pad for engagement with the test strip member.

4. The test device of claim 1 wherein the pad is coupled to a perforated pull tab having an outside edge and an inside edge, the outside edge of the pull tab being lifted and flipped to the opposite side of the sample collection member to position the pad for engagement with the test strip member.

5. The test device of claim 2 wherein the test strip member, the sample collection member, and the window cover are manufactured from solid bleached sulfite (SBS) cardboard.

6. The test device of claim 5 wherein the SBS cardboard has a thickness of about 0.024 inches.

7. An immunochemical-based test device, comprising:

a two-layer center panel, the two-layer center panel having a window in a first layer, a second layer having a repositionable region, such that the first layer is folded over the second layer, wherein a specimen pad is coupled to the repositionable region of the second layer facing and in alignment with the window and having a membrane disposed between the first and second layer between the window opening in the first layer and the specimen pad in the second layer;

a first cover panel, coupled to the two-layered center panel, for covering the window in the two-layer panel; and a second cover panel for receiving a chromatographic member, the second cover panel coupled to the two-layered panel, wherein the repositionable region of the second layer having the specimen application pad is repositionable to an inverted position, the specimen pad forming a face section of the repositionable region allowing a chromatographic member inserted into the second cover member to engage the inverted specimen pad as the second cover member and the two-layered panel are brought in opposition.

8. The test device of claim 7 wherein the repositionable region comprises a perforated pull tab, the pull tab being pivoted from the two-layered center panel forming a pull tab recess area, twisted 180° and reushered into the recessed area to position the pad for engagement with the chromatographic member.

9. The test device of claim 7 wherein the repositionable region comprises a perforated pull tab having an outside edge and an inside edge, the outside edge of the pull tab being lifted and flipped to the opposite side of the two-layer center panel to position the pad in an inverted position for engagement with the chromatographic member.

10. The test device of claim 7 wherein the two-layer center panel, the first cover panel, and the second cover panel are manufactured from solid bleached sulfite (SBS) cardboard.

11. The test device of claim 10 wherein the SBS cardboard has a thickness of about 0.024 inches.

12. An immunochemical-based test device, comprising:

a first panel having a window for insertion of a test strip;

a second panel, coupled to the first panel, the second panel having a window for viewing a test strip inserted into the first panel and the first panel folds over the second panel;

a third panel, coupled to the second panel, the third panel having a repositionable section having a specimen pad coupled to one side, the repositionable section being inverted to expose a collected sample deposited onto the specimen pad to the test strip;

a fourth panel, coupled to the third panel, the fourth panel having a window for applying the test sample to the specimen pad; and a fifth panel, coupled to the fourth panel, the fifth panel for covering the window, and wherein the fifth panel is folded over the fourth panel, and the fourth is brought toward the third panel, with the fifth panel on the outside of the fourth panel.

13. The test device of claim 12 wherein the repositionable section comprises a perforated pull tab, the pull tab being pivoted away from the third panel forming a pull tab recess area, twisted 180° and reushered into the recessed area to position the pad for engagement with the test strip.

14. The test device of claim 12 wherein the repositionable section comprises a perforated pull tab having an outside edge and an inside edge, the outside edge of the pull tab being lifted and flipped to the opposite side of the third panel to position the pad for engagement with the test strip.

15. The test device of claim 12 wherein the fourth panel further comprises a notch for facilitating the repositioning of the repositionable section of the third panel.

16. The test device of claim 12 wherein the first and second panels being further coupled to form a first planar member and the third and fourth panels being further coupled to form a second planar member.

17. The test device of claim 12 wherein the fifth panel further comprises a reusable adhesive for securing the fifth panel over the sample window in the fourth panel.

18. The test device of claim 12 wherein panels are die cut from solid bleached sulfite (SBS) cardboard.

19. The test device of claim 18 wherein the SBS cardboard has a thickness of about 0.024 inches.

20. A method of performing immunochemical-based tests with a device having a first planar member and a second planar member, comprising the steps of:

pulling a cover away from a second planar member, the cover being coupled to the second planar member and folded over the second planar member, the second planar member forming a sample collection member of an integrated assay device housing thereby exposing a sample well formed by a sample panel superimposed over a specimen pad, depositing a sample in the sample well;

closing the cover thereby allowing the integrated assay device housing to be forwarded to a physician or to a laboratory;

lifting a first planar member away from the opposing sample collection member, the first planar member being coupled to the opposing sample collection member and folded over the opposing sample collection member, the first planar member having a test strip insertion well;

installing an immunochromatographic test strip into the test strip insertion well;

repositioning the specimen pad to an inverted position to expose the sample pad to the immunochromatographic test strip;

adding a buffer to the specimen pad to facilitate the interaction between the specimen pad and the immunochromatographic test strip;

bringing the test strip into contact with the specimen pad; and reading the results of the reaction of the sample the test strip.

21. The method of claim 20 wherein the repositioning of the specimen pad further comprises the steps of lifting the specimen pad away from the sample collection member to form a recess area, twisting the tab 180° and lowering the tab into the recessed area to position the pad for engagement with the test strip member.

22. The method of claim 20 wherein the specimen pad is attached to a tab, the tab comprises an outside edge and an inside edge, the positioning of the specimen pad further comprises the steps of lifting the outside edge of the tab and flipping the outside edge of the tab to the opposite side of the sample collection member to position the pad for engagement with the test strip member.

* * * * *